Figure 1:
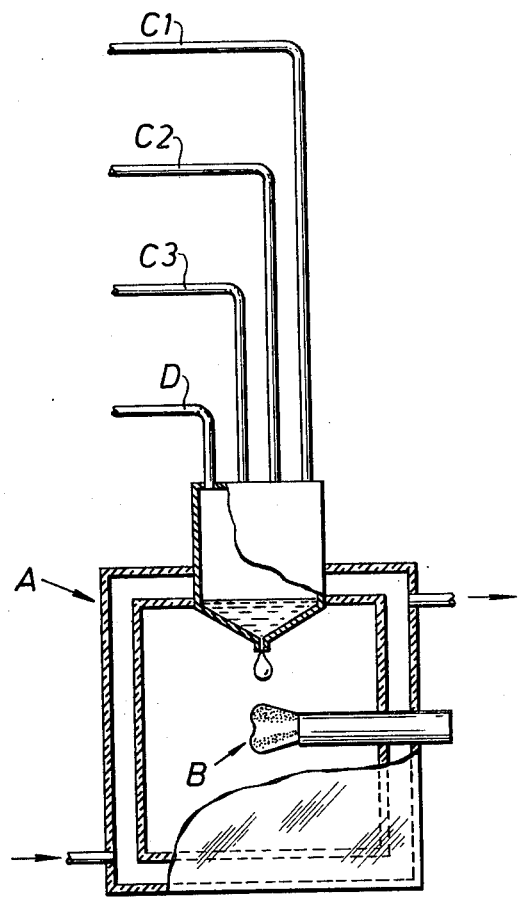

United States Patent [19]

Hernestam et al.

[11] 4,119,711

[45] Oct. 10, 1978

[54] PIPERIDINO DERIVATIVES

[75] Inventors: Sven Erik Harry Hernestam; Nils Arne Nilsson; Curt Harry Nordvi, all of Malmö; Lars-Olof Willard, Höllviksnäs, all of Sweden

[73] Assignee: AB Ferrosan, Malmö, Sweden

[21] Appl. No.: 776,903

[22] Filed: Mar. 11, 1977

[30] Foreign Application Priority Data

Mar. 18, 1977 [GB] United Kingdom ............... 10977/77

[51] Int. Cl.² ................. C07D 221/20; A61K 31/445
[52] U.S. Cl. .................................. 424/54; 260/293.66
[58] Field of Search ...................... 260/293.66; 424/54

[56] References Cited

U.S. PATENT DOCUMENTS

| 3,256,276 | 6/1966 | Grogan et al. | 260/293.66 |
| 3,256,277 | 6/1966 | Rice et al. | 260/293.66 |
| 3,432,499 | 3/1969 | Rice et al. | 260/293.66 |

OTHER PUBLICATIONS

Naylor et al., "Dental Plaque", (1969), pp. 41-45. (A Symposium held in the University of Dundee, Sep. 1969).

Atistrom et al., "J. Peridont. Rev.", vol. 6, pp. 110-114 (1971).

Egelberg, "Odont. Rev.", vol. 16, No. 1, (1965), pp. 31-41.

Pigman et al., "J. Dent. Res.", (1952), pp. 627-633.

*Primary Examiner*—Henry R. Jiles
*Assistant Examiner*—Robert T. Bond
*Attorney, Agent, or Firm*—Haseltine, Lake & Waters

[57] ABSTRACT

Novel spiro 1-(hydroxyalkyl)-piperidino derivatives and acid addition salts thereof, useful in the prevention and treatment of dental caries and periodontitis, are disclosed. Methods of preparing said derivatives, orally acceptable compositions containing said compounds, and a method of treatment therewith are also disclosed.

14 Claims, 3 Drawing Figures

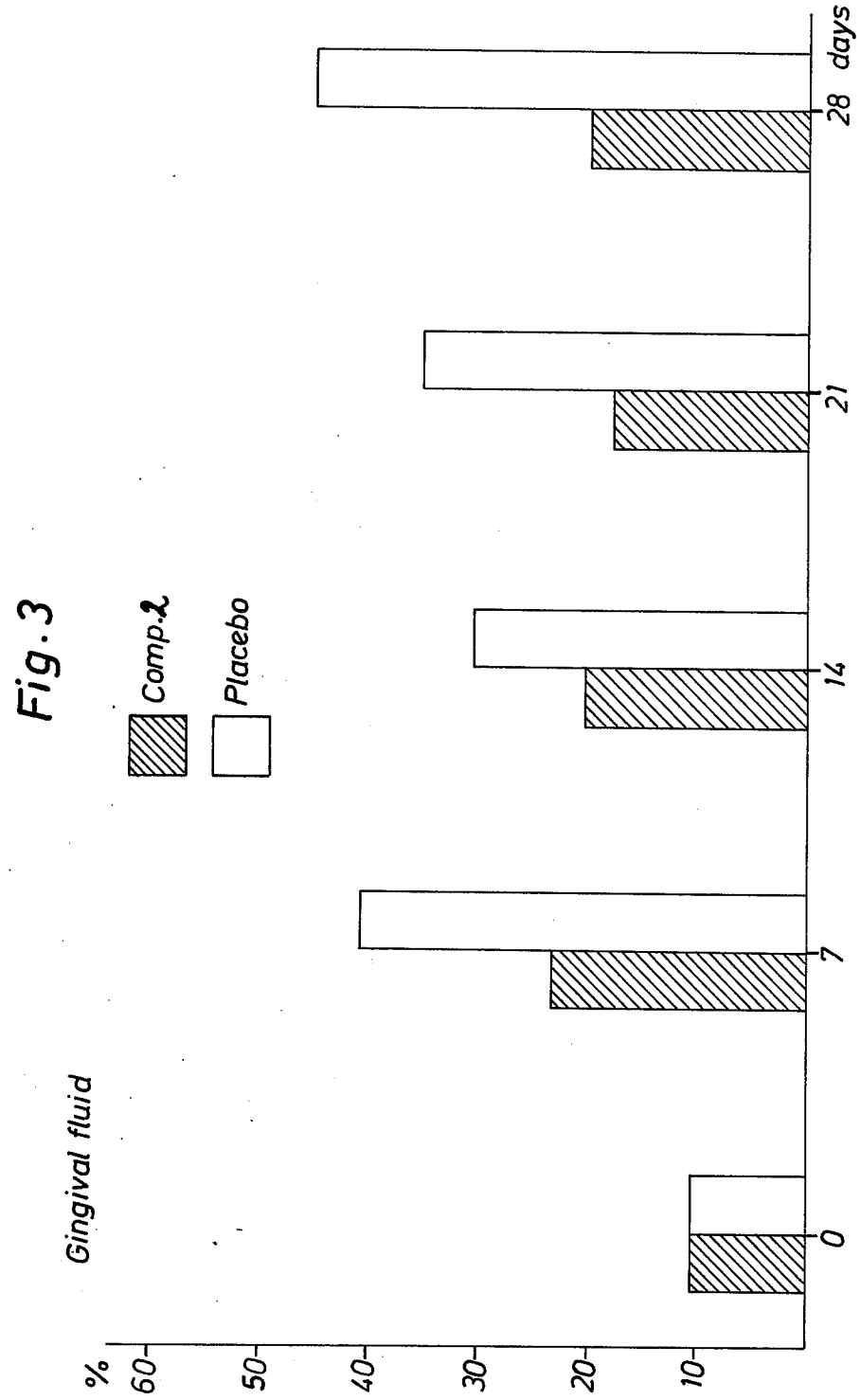

PIPERIDINO DERIVATIVES

The present invention relates to new piperidine derivatives, to processes for their preparation and to compositions containing them.

According to one feature of the present invention there are provided compounds of the general formula

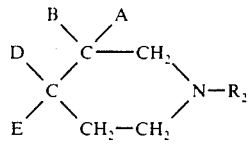   I

[wherein either A and B each represents a hydrogen atom and D and E together represent a group $R_1$ or D and E each represents a hydrogen atom and A and B together represent a group $R_1$, $R_1$ being a straight-chain or branched alkylene group (forming a spiro structure) containing 7 to 16, preferably 8-13, carbon atoms, and $R_2$ represents a straight-chain or branched hydroxyalkyl group containing 2 to 10 carbon atoms, preferably 2-6 carbon atoms].

The sum of the C-atoms in $R_1$ and $R_2$ is preferably from 10 to 17.

The compounds according to the invention have interesting properties which render them useful in the treatment of oral diseases such as periodontitis and dental caries.

The compounds according to the present invention may, for example, be prepared by the following processes, which processes constitute further features of the present invention:

A. by reducing a mono- or di-oxo substituted piperidine of the general formula

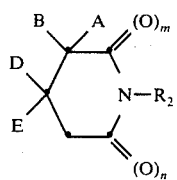   II (wherein A, B, D and E are as herein defined, and $n$ and $m$ each represents 0 or 1 with the proviso that $n$ and $m$ do not both represent 0).

The reduction is preferably performed with lithium aluminium hydride in a solvent such as diethyl ether or tetrahydrofuran. The reaction mixture may then be treated with water and sodium hydroxide and the desired piperidine derivative obtained by distillation.

B. By alkylation of a piperidine derivative of formula

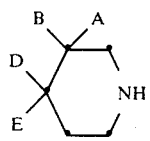   III (wherein A, B, D and E are as hereinbefore defined) for example by reaction with an alkylating agent of formula $R_2X$   IV (wherein $R_2$ is as hereinbefore defined and X represents a leaving group, for example a halogen atom or a sulphonate ester or reactive oxide group) or with an appropriate alkylene oxide.

The reaction is conveniently effected in the presence of an organic solvent, e.g. benzene or xylene. Where a halo-alkanol or organic sulphonate ester of formula III is used as alkylating agent it is preferable to effect the reaction in the presence of an acid binding agent, e.g. triethylamine or potassium carbonate. Alternatively an excess of the compound of formula IV may serve as acid binding agent. The reaction is preferably effected at elevated temperature, e.g. 75° to 150° C., in an autoclave.

C1. By reaction of a compound of the general formula

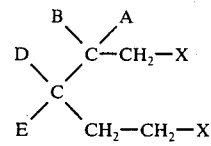   V (wherein A, B, D, E and X are as hereinbefore defined) with an aminoalkanol of the general formula $H_2N \cdot R_2$   VI (wherein $R_2$ is as hereinbefore defined). The reaction is preferably effected at elevated temperature, e.g. 120°-170° C. in an autoclave, advantageously in the presence of an acid binding agent, e.g. triethylamine.

C2. By treatment of a substituted tetrahydropyran of formula

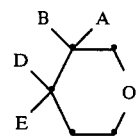   VII (wherein A, B, D and E are as hereinbefore defined) with a compound of formula VI as hereinbefore defined. The reaction is conveniently effected at elevated temperature, e.g. 200°-300° C., in an autoclave.

D. By reaction of a compound of formula

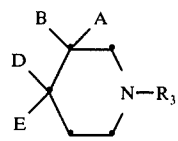   VIII (wherein A, B, D and E are as hereinbefore defined) and $R_3$ is an alkyl group, straight-chain or branched, substituted by a group convertible to or replaceable by a hydroxy or hydroxymethyl group.

Thus, for example, $R_3$ may be substituted by a halogen atom or by a $NH_2$, O-acyl, O-alkyl, O—$CH_2C_6H_5$, COOEt, CN or CHO group or may, for example, be a group —$CO(CH_2)_p$COOEt, wherein $p$ is 0-8.

Di-oxo compounds of formuls II may, for example, be obtained by reaction of a correspondingly substituted glutaric acid of formula

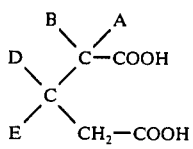

(wherein A, B, D and E are as hereinbefore defined) or its derivatives, e.g. its anhydride, with a compound of formula VI as hereinbefore defined.

The reaction is conveniently performed by heating a mixture of the compounds at 100°–250° C. in an autoclave for 10–20 h without solvent. The yield is better than 75%.

Mono-oxo derivatives of formula II may, for example, be synthesised from correspondingly substituted γ-halovaleric acids by reaction with a compound of formula VI under conditions similar to those described above. Thus, for example, compounds of formula

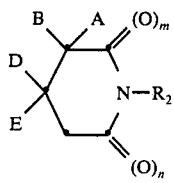

may be synthesised from compounds of formula, e.g.:

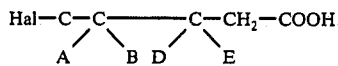

The ring is closed under similar conditions as with IX.

Compounds of formula III may, for example, be prepared by ring closure of correspondingly substituted compounds of formula IX or X by reaction with $NH_3$ or $NH_2CONH_2$ under conditions analogous to those described above. The resulting mono- or di-oxo compounds may then be reduced, for example by means of lithium aluminium hydride as described under reaction A.

Compounds of formula V may, for example, be obtained from compounds of formula

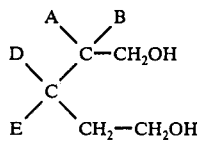

by conventional methods. Thus, for example, compounds of formula V wherein X represents a chlorine atom may be obtained by reacting compounds of formula XI with thionyl chloride.

Compounds of formula XI may themselves be obtained by reduction of correspondingly substituted esters of compounds of formula IX, for example by means of lithium aluminium hydride.

Compounds of formula VII may, for example, be prepared by heating a compound of formula XI with sulphuric acid and subjecting the product to distillation.

Compounds of formula VII may, for example, be synthesised by methods analogous to those described under reaction B. ($NH_2$-groups in the side-chain $R_3$ may be protected by acyl groups).

Halogen atoms in the side-chain $R_3$ may be replaced by O-acyl groups by treatment with silver acetate in acetic acid at 100° C. O-acyl groups may be hydrolysed by alkali.

An HNAc group is hydrolysed to $NH_2$ and the $NH_2$ group is transformed to OH by treatment with $NaNO_2$ in acid solution. —$CH_2C_6H_5$ is removed by catalytic reduction in conventional manner.

The compounds according to the present invention may be incorporated into preparations for dental and/or oral hygiene together with conventional carriers and excipients. Such preparations constitute a further feature of the present invention.

The oral diseases, periodontitis and dental caries, in man appear to be the result of complex biological interactions of various organisms of which the dental plaque is composed. Chronic periodontitis, perhaps the mose common cause of tooth loss, is an inflammatory process of the supporting tissues of the teeth and about as prevalent as dental caries.

The development of tooth diseases has a common cause, viz. the dental plaque. The dental plaque is a deposit upon the surface of a tooth which contains for example food debris which act as a medium for a variable bacterial flora. It leads to a special structure of a harder water-insoluble plaque followed by an onset of both caries and inflammatory periodontal diseases in this region.

In the field of oral and dental hygiene there is a large variety of preparations employed as cleansing and hygienic agents for the oral activity. They may be used in tooth pastes, tablets, etc. A wide variety of chemical and biological agents have been suggested in order to retard dental plaque after it is formed or to protect the teeth against the resulting diseases. However, the mechanical removal of the dental plaque is up to now the most effective method. The chemical approach to plaque inhibition involved different groups of compounds, antibiotics, chemotherapeutics and desinfectants, fluoro compounds, organic phosphatases, chelate-forming compounds, emulsifiers, etc. Some examples are penicillin (antibiotics), chlorhexidine and 8-hydroxyquinoline (desinfectants), ethylenediamine tetraacetate (chelate-forming), NaF (strenghtening of the tooth enamel).

Some of them have too insignificant effects. Others, such as antiseptics and antibiotics, are likely to produce side effects worse than the diseases as such and still others show a certain toxicity, e.g. the fluorine compounds. (NaF may not be used as an antiplaque compound, but under strong supervision as an enamel reinforcing compound.)

It seems clear that the plaque formation is of a very complicated nature and for their chemical removing it is necessary to use compounds having a special chemical structure without pronounced antibacterial effect and having a very low toxicity.

The compounds according to the present invention have been submitted to intensive in vitro and in vivo tests and compared with reference-substances which are clinically used.

The in vitro test is performed in an artificial mouth (FIG. 1).

Artificial mouth

The plaque inhibiting effect has been studied in a so-called Artificial mouth originally described by Pigman et al. (J. dent. Res. 31, 627, 1952), but later on modified (Naylor et al., "Dental Plaque", 1969).

The apparatus (see enclosed FIG. 1) is made of glass and provided with a jacket and several connections (A). One or two extracted human teeth mounted on a glass rod are put in from one side and fixed (B). By peristaltic pumps, a slow-moving flow of substrate, bacteria (Streptococcus mutans) and sterile pooled saliva is supplied dropping down on the fixed tooth surface (C). The space in which the tooth has been put in has a slight overpressure of a mixture of carbon dioxide and nitrogen (D). The temperature inside the vessel is kept constant at 35° C. by means of thermostated water circulating in the jacket.

Many apparatuses can be connected in series.

After 3-4 days, a tooth mounted and treated in this way obtains plaque on its surface. This plaque consists of saliva components, cellular fragments and bacteria.

By taking out the mounted tooth at certain intervals, from the beginning of the test, and treating it with different substances it can be investigated whether the plaque forming is inhibited in its development, i.e. the plaque inhibiting effect.

Tests with out substances have shown that they exert a clear plaque inhibiting effect, much better than chlorohexidine. Chlorohexidine has, besides its antiseptic activity, unwanted side effects, such as colouring of the teeth and development of resistance by continous use. The test results have shown that even after 14 days no plaque has been formed, compare FIG. 2.

TESTS IN VIVO

For tests in vivo of a plaque inhibiting effect, dogs have turned out to be suitable experimental animals (Egelberg: Odont. Revy 16, 31-41, 1965).

The tests have been performed by giving the dogs hard food and several tooth-cleanings during a period of 14 days, after which the dogs have obtained a very good tooth status, i.e. clean teeth without caries; gingival pockets and other membranes of the oral cavity are clinically without objections.

After these weeks of treatment, the real test was started. The dogs were now given soft food and the tooth-cleaning was rejected thereby creating favourable conditions for plaque forming and, later on, tooth decay.

By painting the teeth, both with the compounds, e.g. 2, and so forth and with physiological saline, we could observe to what extent a plaque inhibition set in.

another way to register the plaque forming is to estimate, quantitatively, the increase of gingival fluid in the gingival pockets, which means that the secretion of gingival fluid increases. (Attstrom et al.: J. periodont. Res., Preprint 1971). (FIG. 3).

According to these criteria we have studied the effect of our compounds which has been painted on the tooth surface twice a day during a 4-week-period. As a control on the same dogs we have used physiological saline.

Figure 2:
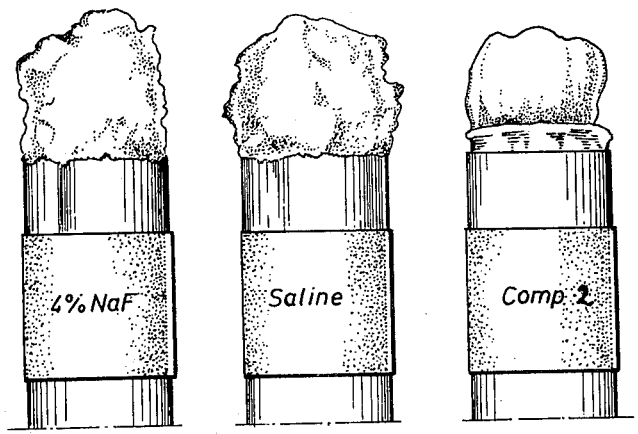

The visual as well as the quantitative estimations of the status of the teeth after treatment show that teeth treated with compound 2 have a significantly lower formation of plaque than the control teeth (FIG. 2).

The novel compounds are preferably obtained and tested as hydrochlorides or hydrofluorides. They are also used in the oral preparations, although the bases or other pharmacologically accepted salts may be used. These salts can be prepared from the bases in conventional methods, e.g. with maleic, fumaric, succinic acids.

The preferred cylinically used formulations are dentifrices, paste or powder, mouth rinses, mouthspray, chewing gum, tablets, etc. In the preparations the compounds may be used in concentrations from 0.1 to 5% and they may also be used together with other pharmacologically active substances, e.g. NaF, 6-n-amyl-m-cresol, 2,4-dichlorobenzyl alcohol.

The invention will be further clarified by the following examples.

EXAMPLE 1

3-aza-3-(3'-hydroxy-propyl)-2,4-dioxo-spiro[5.11]heptadecane

A mixture of 8 g (0.03 moles) of 3,3-undecamethyleneglutaric anhydride, m.p. 130° C. and 3 g (0.04 moles) of 3-amino-1-propanol were heated for 1 hour at 170° C. Water distilled off. The reaction mixture was then distilled at 200°-210° C./0.1 mm Hg. Yield: 8 g of oil. The product was dissolved in a mixture of tetrahydrofuran and ligroin. 7.4 g of white crystals, m.p. 93° C., were obtained.

EXAMPLE 2.

3-aza-3-(3'-hydroxy-propyl)spiro[5.11]heptadecane

An amount of 7 g of 3-aza-3-(3'-hydroxy-propyl)-2,4-dioxo-spiro[5.11]heptadecane in 100 ml of tetrahydrofuran are added under stirring to 10 g of LAH suspension in a mixture of 600 ml of diethyl ether and 100 ml of tetrahydrofuran and the reaction mixture is refluxed for 2.5 h and then decomposed by slow addition of water. The precipitate is filtered off. The ether solution is dried and evaporated. The crystalline residue is recrystallized from ethanol, m.p. 113° C. The base is dissolved in ether and the hydrochloride precipitated with alcoholic hydrochloric acid. After recrystallization the melting point is 240° C., yield 93%.

EXAMPLE 3-13

The procedures according to said general method as described in Example 1 and Example 2 are used for the preparation of the compounds in Table 1.

EXAMPLE 14

3-aza-3-(3'-hydroxy-propyl)-spiro[5.11]heptadecane

A solution of 8 g (0.03 moles) of 3-aza-2,4-dioxo-spiro-[5.11]heptadecane, m.p. 192°-195° C. in 100 ml of tetrahydrofuran is slowly added to 5 g of LAH suspension in 200 ml of diethyl ether (or tetrahydrofuran) and the reaction mixture is refluxed for 24 h and then decomposed by slow addition of water. The precipitate is filtrered off. The ether solution is dried and evaporated. The residue is dissolved in 200 ml of toluene or xylene and 3 g (0.03 moles) of 3-chloro-1-propanol and 5 g of triethylamine is added. The reaction mixture is refluxed for 12 h. The triethylamine hydrochloride is filtered off and the solvent evaporated. The crystalline residue is recrystallized from ethanol, m.p. 131°-134° C. The base is dissolved in ether and the hydrochloride precipitated with alcoholic hydrochloric acid. After recrystallization the melting point is 240°-243° C. Yield 7.6 g (76%).

EXAMPLE 15

Tooth paste

| Ingredients | Amounts per cent |
| --- | --- |
| Compound 2 | 20% |
| Dicalcium phosphate | 50% |
| Sorbitol | 6% |
| Glycerol | 18% |
| Na-carboxymethylcellulose | 2% |
| Na-lauryl sulphate | 1% |
| Na-saccharin | 0.1% |
| Peppermint oil | 0.9% |
| Water | up to 100% |

EXAMPLE 16

Chewing gum

| | Amounts per cent |
| --- | --- |
| Core | |
| Compound 2 | 20% |
| Fructose | 50% |
| Glycerol | 5% |
| Mannitol | 30% |
| Gum base | 2% |
| Carboxymethylcellulose | 10% |
| Sodium cyclamate | 1% |
| Carnauba wax. with | |
| Coating | |
| Fructose | 9% |
| Gum arabic | 5% |
| Dextrin | 2% |
| Flavour | 2% |

(The core materials are mixtured at 50° C.)

EXAMPLE 17

A chewable tablet

| | |
| --- | --- |
| Compound 2 | 20% |
| Sorbitol | 800% |
| Potato starch | 150% |
| 5% aq. sol. of gelatin | 30% |
| Peppermint oil | — |
| Na-cyclamate | 2% |
| Na-saccharin | 1% | are tabletted to 1000 tablets with 2% of compound 2.

EXAMPLE 18

Mouth rinse liquid

| | |
| --- | --- |
| Compound 2 | 1% |
| Glycerol | 10% |
| Ethanol | 15% |
| Tween 80 | 0.1% |
| Na-cyclamate | 1.0% |
| Na-saccharin | 0.1% |
| Menthol-flavour | 0.1% |
| Water | ad 100 |

Table 1

$$R_1 \diagup\hspace{-1em}\bigcirc\hspace{-1em}\diagdown N-R_2, HCl$$

| Compound No. | $R_1$ | $R_2$ | M.p. of the hydrochloride ° C | Plaque inhibiting effect |
| --- | --- | --- | --- | --- |
| 2 | $-(CH_2)_{11}-$ | $CH_2CH_2CH_2OH$ | 240 | +++ |
| 3 | $-(CH_2)_{11}-$ | $CH_2CH_2OH$ | 220 | +++ |
| 4 | $-(CH_2)_9-$ | $CH_2CH_2CH_2CH_2OH$ | 230 | (+) |
| 5 | $-(CH_2)_{10}-$ | $CH_2CH_2CH_2OH$ | 250 | + |
| 6 | $-(CH_2)_8-$ | $CH_2CH_2CH_2OH$ | 257-259 | + |
| 7 | $-(CH_2)_8-$ | $CH_2CH_2CH_2CH_2OH$ | 227-229 | + |
| 8 | $-(CH_2)_{13}-$ | $CH_2CH_2OH$ | 208 | ++ |
| 9 | $-(CH_2)_{13}-$ | $CH_2CH_2CH_2OH$ | 215 | + |
| 10 | $-(CH_2)_7-$ | $CH_2CH_2CH_2OH$ | 255 | (+) |
| 11 | $-(CH_2)_8-$ | $CH_2CH_2OH$ | 240-242 | ++ |
| 12 | $-(CH_2)_{12}-$ | $CH_2CH_2CH_2OH$ | 216-218 | ++ |
| 13 | $-(CH_2)_{12}-$ | $CH_2CH_2CH_2CH_2OH$ | 229-231 | ++ |

+++ = very good activity
++ = good activity
+ = fair activity
(+) = weak activity

We claim:

1. A piperidine compound of the formula $$\text{(I)}$$

wherein A and B each represents a hydrogen atom and D and E together represent a group $R_1$, $R_1$ being selected from the group consisting of unsubstituted straight-chain and unsubstituted branched-chain alkylene groups (forming a spiro compound) having 7-16 carbon atoms and $R_2$ is selected from the group consisting of unsubstituted straight-chain and unsubstituted branched-chain hydroxyalkyl groups having 2-10 carbon atoms, and acid addition salts thereof.

2. A compound according to claim 1, wherein $R_1$ has 8-13 carbon atoms.

3. A compound according to claim 1, wherein $R_2$ has 2-6 carbon atoms.

4. A compound according to claim 1, wherein $R_1$ is $-(CH_2)_{11}-$ and $R_2$ is $-CH_2CH_2CH_2OH$.

5. A compound according to claim 1, wherein $R_1$ is $-(CH_2)_{11}-$ and $R_2$ is $-CH_2CH_2OH$.

6. A piperidine compound of the formula $$\text{(I)}$$

wherein D and E each represents a hydrogen atom and A and B together represent a group $R_1$, $R_1$ being selected from the group consisting of unsubstituted straight-chain and unsubstituted branched-chain alkylene groups (forming a spiro compound) having 7-16 carbon atoms and $R_2$ is selected from the group consisting of unsubstituted straight-chain and unsubstituted branched-chain hydroxyalkyl groups having 2-10 carbon atoms, and acid addition salts thereof.

7. A compound according to claim 6, wherein $R_1$ has 8-13 carbon atoms.

8. A compound according to claim 6, wherein $R_2$ has 2-6 carbon atoms.

9. A compound according to claim 6, wherein $R_1$ is $-(CH_2)_{11}-$ and $R_2$ is $-CH_2CH_2CH_2OH$.

10. A compound according to claim 6, wherein $R_1$ is $-(CH_2)_{11}-$ and $R_2$ is $-CH_2CH_2OH$.

11. An oral and dental hygiene composition suitable for use in the treatment of dental caries and periodontitis, comprising a compound of claim 1, in an amount effective for said purpose, in association with an orally acceptable carrier.

12. An oral and dental hygiene composition suitable for use in the treatment of dental caries and periodontitis, comprising a compound of claim 6, in an amount effective for said purpose, in association with an orally acceptable carrier.

13. A process for prevention and treatment of dental caries and periodontitis, wherein the oral cavity including the tooth surfaces at least daily are treated with a solution of from 0.1 to 5% by weight of a compound of claim 1.

14. A process for prevention and treatment of dental caries and periodontitis, wherein the oral cavity including the tooth surfaces at least daily are treated with a solution of from 0.1 to 5% by weight of a compound of claim 6.

* * * * *